United States Patent
Lupienski et al.

(10) Patent No.: US 10,274,448 B2
(45) Date of Patent: Apr. 30, 2019

(54) METHOD AND APPARATUS FOR EVALUATING A WELD JUNCTION BETWEEN A TERMINAL AND AN ELECTRODE ELEMENT OF A BATTERY CELL

(71) Applicant: GM GLOBAL TECHNOLOGY OPERATIONS LLC, Detroit, MI (US)

(72) Inventors: Jason A. Lupienski, Birmingham, MI (US); Robert W. Chalfant, Berkley, MI (US); James E. Kettlewell, Windsor (CA)

(73) Assignee: GM Global Technology Operations LLC, Detroit, MI (US)

( * ) Notice: Subject to any disclaimer, the term of this patent is extended or adjusted under 35 U.S.C. 154(b) by 238 days.

(21) Appl. No.: 15/294,111

(22) Filed: Oct. 14, 2016

(65) Prior Publication Data
US 2017/0322168 A1    Nov. 9, 2017

Related U.S. Application Data

(60) Provisional application No. 62/332,662, filed on May 6, 2016.

(51) Int. Cl.
*G01N 27/20* (2006.01)
*H01M 2/26* (2006.01)
*H01M 10/04* (2006.01)

(52) U.S. Cl.
CPC .............. *G01N 27/20* (2013.01); *H01M 2/26* (2013.01); *H01M 10/04* (2013.01)

(58) Field of Classification Search
CPC ......... G01N 27/20; H01M 2/26; H01M 10/04
See application file for complete search history.

(56) References Cited

U.S. PATENT DOCUMENTS

| | | | |
|---|---|---|---|
| 6,218,846 B1* | 4/2001 | Ludwig | G01R 1/07342 324/713 |
| 2012/0290228 A1* | 11/2012 | Lev | G01N 27/041 702/58 |
| 2013/0029206 A1* | 1/2013 | Lev | H01M 2/206 429/161 |

FOREIGN PATENT DOCUMENTS

| | | |
|---|---|---|
| CN | 102778608 A | 11/2012 |
| CN | 102778616 A | 11/2012 |
| CN | 105403803 A | 3/2016 |
| JP | 109196881 A | 7/1997 |

(Continued)

OTHER PUBLICATIONS

Lev, New Areas of Automotive NDE: Li-ion Batteries and Composite Materials, Mar. 1, 2012.*

(Continued)

*Primary Examiner* — Daniel R Miller
(74) *Attorney, Agent, or Firm* — Quinn IP Law

(57) ABSTRACT

A method and a test fixture for evaluating a weld seam joining an electrode foil element and a terminal of a battery cell include segmenting the weld seam joining the electrode foil element and the terminal into a plurality of zones. For each of the zones, an electrical current is applied between the terminal and the electrode foil element in the zone, and a resistance is determined across the terminal and the electrode foil element in the zone. Integrity of the weld seam is evaluated for each of the zones based upon the resistance between the terminal and the electrode foil element in the zone.

19 Claims, 2 Drawing Sheets

(56) References Cited

FOREIGN PATENT DOCUMENTS

KR      1020110109579 A     10/2011

OTHER PUBLICATIONS

Langan et al., A Guide to Low Resistance Testing, available at http://www.testequipmentdepot.com/megger/pdf/low-resistance-testing.pdf on Apr. 8, 2004.*

DLRO-10X product brochure, available at https://www.techrentals.com.my/pdf/products/Megger_DLRO_10X_Digital_Microhmmeter.pdf on Oct. 30, 2003.*

\* cited by examiner

METHOD AND APPARATUS FOR EVALUATING A WELD JUNCTION BETWEEN A TERMINAL AND AN ELECTRODE ELEMENT OF A BATTERY CELL

CROSS-REFERENCE TO RELATED APPLICATIONS

This application claims the benefit of U.S. Provisional Patent Application No. 62/332,662 filed on May 6, 2016, the disclosure of which is hereby incorporated by reference.

INTRODUCTION

A battery pack typically includes multiple rechargeable battery cells that are connected in series or parallel to store and supply electric power to a distribution system. Each battery cell includes a plurality of electrode foils having alternately-placed positive and negative charge portions. The electrode foils are separated by separator material and enclosed within a sealed outer pouch that is filled with an electrolyte solution. The separator material, e.g., polyethylene and/or polypropylene film, helps prevent an electrical short condition while permitting the free transfer of electrical charge between electrode foils.

Positive and negative terminals may be welded to corresponding positive and negative electrode foils. Process capability of the welding process that forms the internal weld may be subject to variation due to welder variations and other factors.

SUMMARY

A method and a test fixture for evaluating a weld seam joining an electrode foil element and a terminal of a battery cell are described. This includes segmenting the weld seam joining the electrode foil element and the terminal into a plurality of zones. For each of the zones, an electrical current is applied between the terminal and the electrode foil element in the zone, and a resistance is determined across the terminal and the electrode foil element in the zone. Integrity of the weld seam is evaluated for each of the zones based upon the resistance between the terminal and the electrode foil element in the zone.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which.

DETAILED DESCRIPTION

Figure 1:
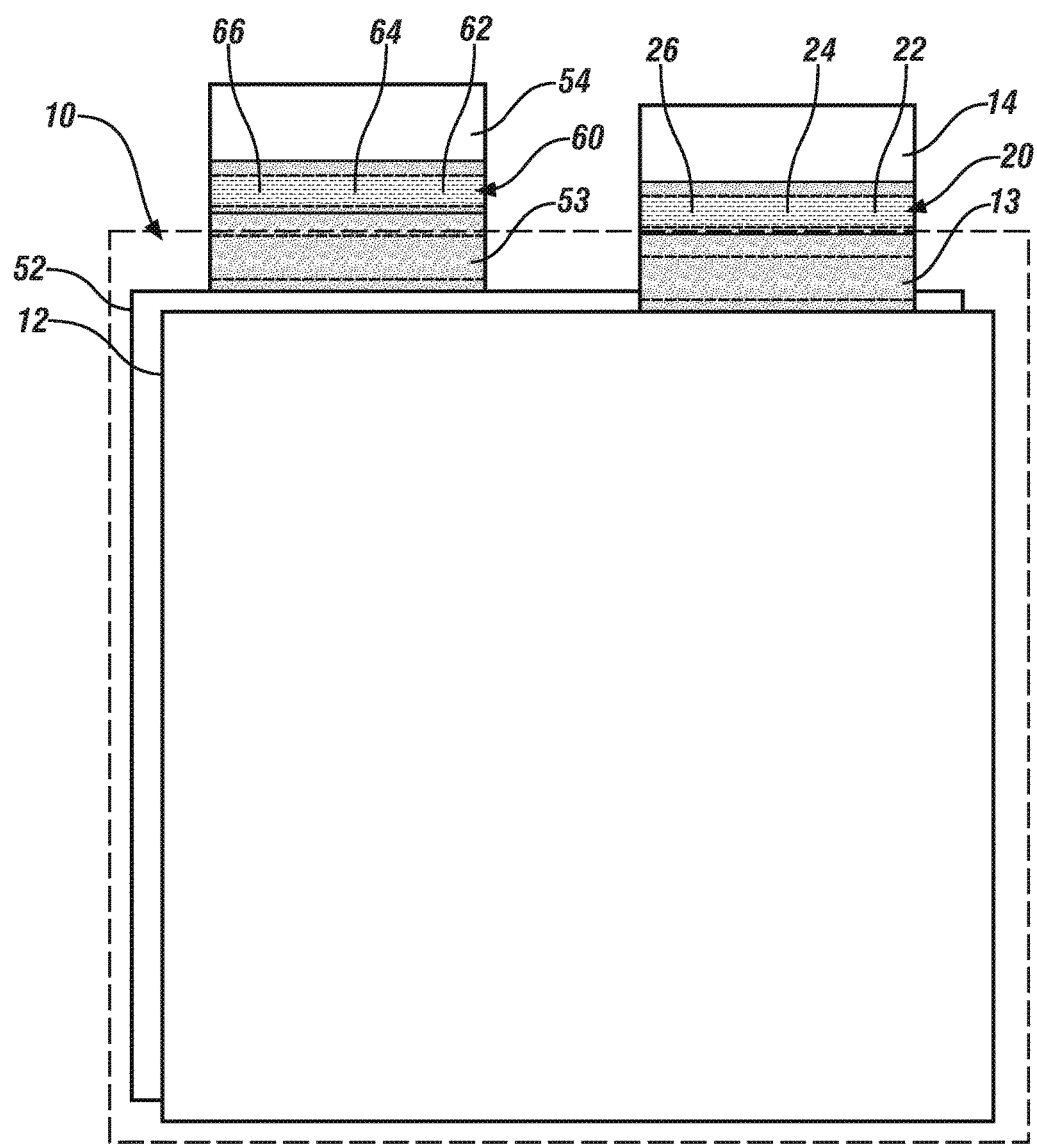
FIG. 1 schematically illustrates a front view of selected elements of a single battery cell, in accordance with the disclosure.

Referring now to the drawings, which are provided for the purpose of illustrating certain exemplary embodiments only and not for the purpose of limiting the same, FIG. 1 schematically illustrates a front plan view of selected elements of a single battery cell 10. Like numerals indicate like or corresponding parts throughout the several views. Those having ordinary skill in the art will recognize that terms such as "horizontal", "vertical", "above," "below,", "top," "bottom," etc., are used descriptively for the figures, and do not represent limitations on the scope of the disclosure, as defined by the appended claims.

The battery cell 10 includes a plurality alternating positive electrode foils 12 and negative electrode foils 52 that are fabricated in plate form and arranged in a vertical stack that is contained within a sealed pouch (not shown) that is filled with electrolytic fluid in one embodiment. A single positive electrode foil 12 and a single negative electrode foil 52 are shown for ease of illustration. The positive electrode foils 12 may be fabricated from copper and the negative electrode foils 52 may be fabricated from aluminum in one embodiment. The positive electrode foil 12 includes a tab portion 13 that projects upwardly as shown, and is welded to a positive terminal 14, forming a first weld seam 20. The first weld seam 20 may be in the form of a lap junction that mechanically and electrically joins the tab portion 13 and the positive terminal 14. Likewise, the negative electrode foil 52 includes a tab portion 53 that projects upwardly as shown, and is welded to a negative terminal 54 forming a second weld seam 60. The second weld seam 60 may also be in the form of a lap junction that mechanically and electrically joins the tab portion 53 and the negative terminal 54. Other details related to the battery cell 10 are known to one of ordinary skill in the art. In one embodiment, the single battery cell 10 is configured as a lithium-ion battery cell that is rechargeable, although the concepts described herein may be applied to other battery cell configurations that are fabricated in a manner described herein. Suitable battery technologies may include, for example, lead-acid, nickel-metal hydride (NiMH), lithium-ion (Li-Ion), Li-Ion polymer, lithium-air, nickel-cadmium (NiCad), valve-regulated lead-acid (VRLA) including absorbed glass mat (AGM), nickel-zinc (NiZn), molten salt (ZEBRA battery), nickel manganese cobalt (NMC), lithium iron phosphate (LFP), lithium manganese oxide (LMO), as well as other suitable battery technologies and/or combinations thereof.

The first and second weld seams 20, 60 are depicted as being horizontal, and preferably extend completely across a width of the corresponding tab portion 13, 53. The first and second weld seams 20, 60 are described as being the form of a lap weld junction, although the concepts described herein are not so limited. The first and second weld seams 20, 60 may be formed in any suitable junction configuration, and may be formed by any suitable welding technology, including, by way of non-limiting examples, ultrasonic welding, laser welding, ion-beam welding, resistance welding, friction welding, etc. The first and second weld seams 20, 60 may be nominally divided into a plurality of zones for purposes of evaluation, wherein the zones are nominal constructs that represent identified portions of the respective weld seam. By way of non-limiting example, the first weld seam 20 may be separated into three zones, including a left zone 26, a center zone 24 and a right zone 22. Likewise, the second weld seam 60 may be separated into three zones, including a left zone 66, a center zone 64 and a right zone 62. The quantity of zones may be any suitable number, and the names of the zones may be any suitable moniker.

The battery cell 10 is described as a plurality of alternating positive electrode foils 12 and negative electrode foils 52 that are fabricated in plate form and arranged in a vertical stack. Alternatively, the battery cell 10 may be configured as a cylindrical device having terminals extending from one of its ends. Alternatively, the battery cell 10 may be configured as a brick-shaped device having terminals extending from one of its ends. The concepts described herein apply to any geometric configuration of the battery cell 10.

A battery assembly may be composed of a plurality of individual constituent battery cells. The battery assembly or constituent cells may be configured to provide an amount of electric power sufficient to operate a variety of systems associated with a vehicle including, for example, vehicle drivetrain systems. Individual battery cells may be electrically connected to form a battery cell group. In certain embodiments, a plurality of battery cell groups may be incorporated in a battery module. A plurality of battery modules may be similarly included in one or more battery units of a battery assembly. In certain embodiments, individual battery cells included in a battery assembly may comprise prismatic pouch battery cells. Individual battery cells may be arranged in a stack configuration, and may include tabs forming battery cell terminals that may be suitably electrically connected for provision of electrical power to loads and/or for charging and/or discharging of the battery cells. In some embodiments, a plurality of individual battery cells may be electrically connected in parallel via associated tabs to form a battery cell group. A plurality of battery cell groups may be electrically connected in series via one or more common buses, such as L-shaped channels, to form a battery module included in a battery pack.

Figure 2:
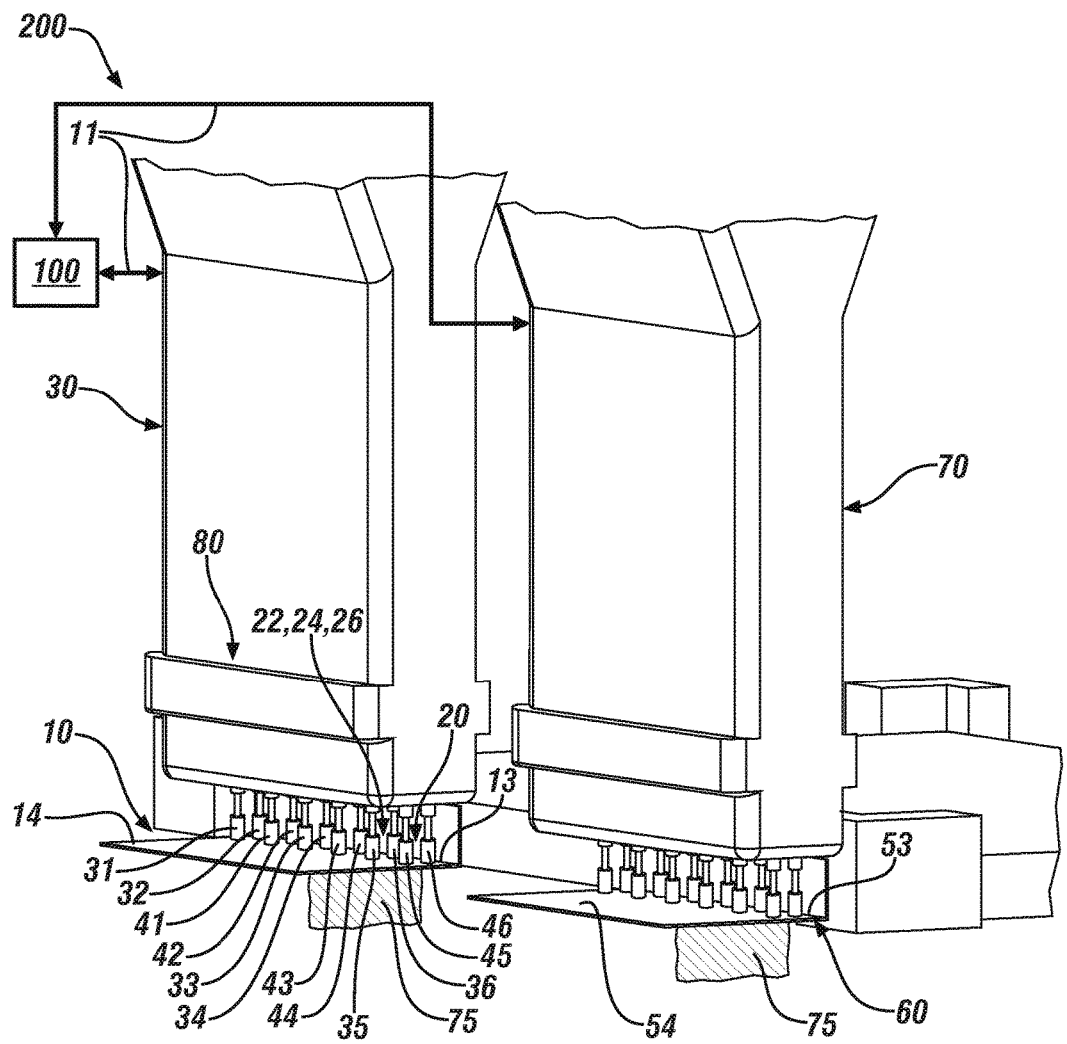
FIG. 2 schematically shows a partial isometric view of selected elements of a test fixture for evaluating weld seams associated with positive and negative terminals of a battery cell, in accordance with the disclosure.

FIG. 2 schematically shows an embodiment of a test fixture 200 for evaluating weld seams on a workpiece, wherein the workpiece is an embodiment of the battery cell 10 described with reference to FIG. 1 and the weld seams include the first weld seam 20 that is disposed to join the tab portion 13 and the positive terminal 14, and the second weld seam 60 that is disposed to join the tab portion 53 and the negative terminal 54. The test fixture 200 includes a base 75, first and second end effectors 30, 70, respectively, and a controller 100. The term "end effector" is any device that may be controlled to accomplish a pre-defined task in response to a control command, and may be mechanically actuated, electro-mechanically actuated, pneumatically actuated, or may employ another actuation system. As shown, the battery cell 10 is arranged in a horizontal orientation with the positive terminal 14 located on the leftward side and the negative terminal 54 located on the rightward side.

The first and second end effectors 30, 70 are preferably identical devices that are configured to evaluate either the first weld seam 20 or the second weld seam 60. The first end effector 30 is now described in detail. One of ordinary skill in the art appreciates that the description associated with the first end effector 30 applies to the second end effector 70.

The first end effector 30 is configured to individually evaluate the left zone 26, center zone 24 and right zone 22 of the weld seam 20. The first end effector 30 includes a plurality of current probes and corresponding voltage probes that can electrically connect to an electrical test circuit 80 as described herein to evaluate integrity of the weld seam 20.

The current probes and voltage probes are preferably fabricated from a material that is similar to the material of the respective terminal so as to not introduce signal distortion due to coupling of dissimilar metals. The first end effector 30 may be advantageously placed into physical contact with the tab portion 13 and the positive terminal 14 across the first weld seam 20 in proximity of one of the left zone 26, center zone 24 or right zone 22 of the first weld seam 20. As shown, paired current probes 31 and 32 are disposed to straddle the first weld seam 20 in proximity of the right zone 22, and corresponding paired voltage probes 41 and 42 are disposed to straddle the first weld seam 20 adjacent thereto. The current probe 31 and voltage probe 41 are disposed to contact the positive terminal 14, and the current probe 32 and voltage probe 42 are disposed to contact the tab portion 13. Paired current probes 33 and 34 are disposed to straddle the first weld seam 20 in proximity of the center zone 24, and corresponding paired voltage probes 43 and 44 are disposed to straddle the first weld seam 20 adjacent thereto in like manner to those described for the right zone 22. Paired current probes 35 and 36 are disposed to straddle the first weld seam 20 in proximity of the left zone 26, and corresponding paired voltage probes 45 and 46 are disposed to straddle the first weld seam 20 adjacent thereto in like manner to those described for the right zone 22. The second end effector 70 is configured similar to the first end effector 30 to individually evaluate the left zone 66, center zone 64 and right zone 62 of the weld seam 60.

Figure 3:
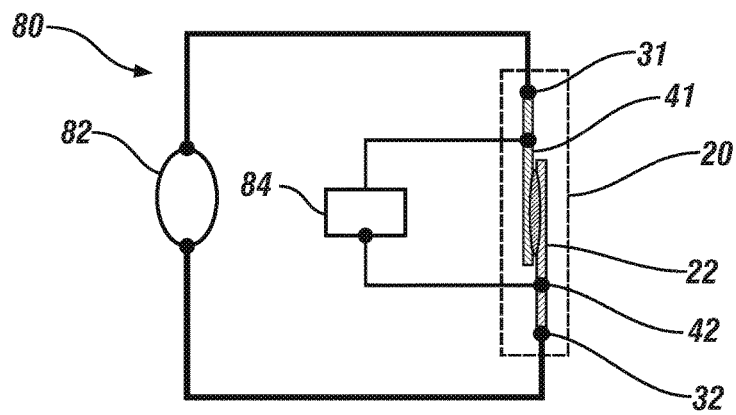
FIG. 3 schematically shows an embodiment of an electrical test circuit that electrically connects to a plurality of current probes and corresponding voltage probes that may be disposed in a test fixture to evaluate weld seams associated with positive or negative terminals of a battery cell, in accordance with the disclosure.

FIG. 3 schematically shows an embodiment of an electrical test circuit 80 that electrically connects to a plurality of current probes and corresponding voltage probes. As shown, the current probes include paired current probes 31 and 32, and the voltage probes include paired voltage probes 41 and 42, which are associated with the right zone 22 of the first weld seam 20. Although not shown, the electrical test circuit 80 preferably includes a multiplexed power supply and data acquisition system that also electrically connects to paired current probes 33 and 34 and paired voltage probes 43 and 44 that are associated with the center zone 24 of the first weld seam 20 and further electrically connects to paired current probes 35 and 36 and paired voltage probes 45 and 46 that are associated with the left zone 26 of the first weld seam 20.

The electrical test circuit 80 includes a constant current power supply 82 and a data acquisition system 84. The constant current power supply 82 is electrically connected to the paired current probes 31 and 32, and is preferably configured to supply electrical power at a constant electrical current level, e.g., 10 A, across the paired current probes 31 and 32 when they are in physical contact with the positive terminal 14 and the tab portion 13, respectively, across the first weld seam 20 in the right zone 22. The data acquisition system 84 includes an analog/digital converter and related electrical circuits to monitor electrical power across the paired voltage probes 41 and 42 to determine an impedance associated thereacross. The paired voltage probes 41 and 42, analog/digital converter and related electrical circuits are selected to have a capability of measuring electrical parameters that may result in impedance levels in the order of magnitude of micro-ohms.

Referring again to FIG. 2, the controller 100 preferably includes instruction sets, control routines and information from sensors and actuators to evaluate an embodiment of the battery cell 10 described with reference to FIG. 1, including evaluating one or both of the weld seams 20, 60 that join electrode foil elements 12, 52 to the respective positive and negative terminals 14, 54. This preferably includes segmenting the weld seams 20, 60 into a plurality of zones, as previously described. The left zone 26, center zone 24 and right zone 22 are implemented in the first end effector 30, and the left zone 66, center zone 64 and right zone 62 are implemented in the second end effector 60. When the battery cell 10 is placed in the test fixture 200 for evaluation, the positive and negative terminals 14, 54 are oriented to permit interaction with the first and second end effectors 30, 70, respectively. The positive and negative terminals 14, 54 are placed on top of the base 75, and the controller 100 commands the test fixture 200 to position the first and second end effectors 30, 70 to compress the respective positive and negative terminals 14, 54 against the base 75 such that the paired current probes and the paired voltage probes straddle the respective weld seams 20, 60. With reference specifically to the first end effector 30, once it is positioned, the controller 100 commands the constant current power supply 82 to supply electrical power at a constant electrical current level, e.g., 10 A, across the paired current probes 31 and 32, 33 and 34, and 35 and 36. The controller 100 simultaneously monitors voltage potential across the respective paired voltage probes 41 and 42, 43 and 44, and 45 and 46. The controller 100 executes control routines to calculate a resistance value for each of the left zone 26, center zone 24 and right zone 22. The controller 100 evaluates the integrity of the weld seam 20 for each of the left zone 26, center zone 24 and right zone 22 based upon the resistance. The controller 100 can detect a fault in one of the left zone 26, center zone 24 and right zone 22 when the resistance in the respective zone is greater than a threshold resistance. In one embodiment, the threshold resistance correlates to a minimum threshold tensile strength for the zone of the weld seam 20, i.e., a minimum threshold tensile strength for each of the left zone 26, center zone 24 and right zone 22. Magnitudes of the threshold resistance and its correlation to minimum threshold tensile strengths are application-specific, and may be developed as part of process and product development. The controller 100 can command operation of the second end effector 70 in a similar manner.

In one embodiment, the controller 100 can include an instruction set for monitoring the resistance that includes a form of electrochemical impedance spectroscopy (EIS), which may include applying an excitation signal in the form of a small amplitude AC current that is applied across the paired current probes 31 and 32, 33 and 34, and 35 and 36, and measuring current flow across the respective paired voltage probes 41 and 42, 43 and 44, and 45 and 46. Monitoring impedance employing EIS or other similar methods preferably includes applying a current of known magnitude and monitoring voltage, and determining a magnitude for impedance based upon the relationship between current, voltage, and impedance, i.e., V=I*R. In one embodiment, the applied current may be in the form of a sine wave current, and the output signal may thus be a sine wave voltage that is shifted in phase. The amplitude and amount of phase shift of the output signal in combination with the applied current may be evaluated to determine the magnitude of the impedance. Other details related to monitoring impedance of the battery cell 10 employing EIS or other similar methods are known to one of ordinary skill in the art.

The concepts described herein provide opportunity for development of a non-destructive weld test and a related fixture that permits evaluating 100% of the battery cells for internal weld tab conformance during battery assembly processes. This further facilitates a consistent characterization of weld joints across of different zones. In one embodiment, the concepts may facilitate correlating the resistance and mechanical pull strength.

The terms controller, control module, module, control, control unit, processor and similar terms refer to any one or various combinations of Application Specific Integrated Circuit(s) (ASIC), electronic circuit(s), central processing unit(s), e.g., microprocessor(s) and associated non-transitory memory component in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean any controller-executable instruction sets including calibrations and look-up tables. Each controller executes control routine(s) to provide desired functions, including monitoring inputs from sensing devices and other networked controllers and executing control and diagnostic instructions to control operation of actuators. Routines may be executed at regular intervals, or in response to occurrence of a triggering event. Communication between controllers, and communication between controllers, actuators and/or sensors may be accomplished using a direct wired point-to-point link, a networked communication bus link, a wireless link or any other suitable communication link, and is indicated by line 11. Communication includes exchanging data signals in any suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to any physically discernible indicator that conveys information, and may be any suitable waveform (e.g., electrical, optical, magnetic, mechanical or electromagnetic), such as DC, AC, sinusoidal-wave, triangular-wave, square-wave, vibration, and the like, that is capable of traveling through a medium.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

The invention claimed is:

1. A method for evaluating a continuous weld seam joining an electrode foil element and a terminal of a battery cell, the method comprising:
 segmenting the continuous weld seam joining the electrode foil element and the terminal into a plurality of nominal zones;
 simultaneously applying an electrical current between the terminal and the electrode foil element in each of the nominal zones, wherein the applied electrical current is in the form of a sine wave;

determining a resistance across the terminal and the electrode foil element in each of the nominal zones employing an electrochemical impedance spectroscopy method; and evaluating integrity of the weld seam for each of the nominal zones based upon the resistance between the terminal and the electrode foil element in the respective nominal zone.

2. The method of claim 1, wherein evaluating the integrity of the weld seam for each of the zones comprises detecting a fault in the weld seam in the zone when the resistance for the respective zone is greater than a threshold resistance.

3. The method of claim 2, wherein the threshold resistance correlates to a minimum threshold tensile strength of the respective zone of the weld seam.

4. The method of claim 1, wherein applying a current comprises applying a constant current between the terminal and the electrode foil element in the zone.

5. The method of claim 1, wherein the weld seam joins a tab portion of the electrode foil element and the terminal.

6. The method of claim 1, wherein the weld seam comprises an ultrasonically-formed weld seam.

7. The method of claim 1, wherein the weld seam comprises a laser-formed weld seam.

8. The method of claim 1, wherein the weld seam comprises an ion-beam weld seam.

9. The method of claim 1, wherein the weld seam comprises a resistance-formed weld seam.

10. A test fixture for evaluating a weld seam that joins a tab portion of an electrode foil element of a battery cell and a terminal, the test fixture comprising:

an end effector including an electrical test circuit including a current source electrically connected to a plurality of paired current probes and a data acquisition system electrically connected to a plurality of paired voltage probes, wherein the plurality of paired voltage probes and the plurality of paired current probes are disposed to straddle the weld seam in a plurality of zones when the end effector compressively engages the terminal of the battery cell;

a controller, in communication with the electrical test circuit and the data acquisition system of the end effector, the controller including an instruction set, the instruction set being executable to:

simultaneously apply, via the plurality of paired current probes, an electrical current between the terminal and the electrode foil element in each of the zones, and determine a resistance across the terminal and the electrode foil element in each of the zones, and evaluate integrity of the weld seam for each of the zones based upon the resistance between the terminal and the electrode foil element in the zone.

11. The test fixture of claim 10, wherein the instruction set executable to evaluate the integrity of the weld seam for each of the zones comprises the instruction set executable to detect a fault in the weld seam in the zone when the resistance for the respective zone is greater than a threshold resistance.

12. The test fixture of claim 11, wherein the threshold resistance correlates to a minimum threshold tensile strength of the respective zone of the weld seam.

13. The test fixture of claim 10, wherein the instruction set executable to apply a current comprises the instruction set executable to apply a constant current between the terminal and the electrode foil element in the zone.

14. The test fixture of claim 10, wherein the weld seam joins a tab portion of the electrode foil element and the terminal.

15. The test fixture of claim 10, wherein the weld seam comprises an ultrasonically-formed weld seam.

16. The test fixture of claim 10, wherein the weld seam comprises a laser-formed weld seam.

17. The test fixture of claim 10, wherein the weld seam comprises an ion-beam weld seam.

18. The test fixture of claim 10, wherein the weld seam comprises a resistance-formed weld seam.

19. The test fixture of claim 10, wherein the applied electrical current is in the form of a sine wave, and wherein the resistance across the terminal and the electrode foil element in each of the nominal zones is determined employing electrochemical impedance spectroscopy.

* * * * *